United States Patent [19]

De Jager

[11] 4,378,356
[45] Mar. 29, 1983

[54] MULTI-PHASE COMBINATION-TYPE SEQUENTIAL PREPARATION FOR ORAL CONTRACEPTION AND METHOD OF ORAL CONTRACEPTION

[75] Inventor: Evert De Jager, Oss, Netherlands

[73] Assignee: Akzon N.V., Oss, Netherlands

[21] Appl. No.: 244,071

[22] Filed: Mar. 16, 1981

[30] Foreign Application Priority Data

Mar. 18, 1980 [NL] Netherlands ........................ 8001593

[51] Int. Cl.³ ............................................. A61K 31/56
[52] U.S. Cl. ..................................... 424/238; 424/239
[58] Field of Search ........................ 424/238, 239, 243

[56] References Cited

U.S. PATENT DOCUMENTS 3,409,721  11/1968  Applezweig ........................ 424/238
3,957,982   5/1976  Lachnit-Fixon et al. ........... 124/238
4,018,919   4/1977  Black ................................... 424/243

*Primary Examiner*—Elbert L. Roberts
*Attorney, Agent, or Firm*—Abelman, Frayne & Rezac

[57] ABSTRACT

The invention relates to a multiphase combination-type sequential preparation for oral contraception consisting of 20-22 tablets each containing a gestagen and an oestrogen wherein a first phase consists of 5-8 tablets, each of which contains a low dose of gestagen and a relatively high dose of oestrogen, a second phase of 5-8 tablets each having a gestagen dose which is greater than that during the first phase and an oestrogen dose which is smaller than that in the first phase, and a third phase of 5-11 tablets each of which has a gestagen dose equal to or greater than that during the second phase and an oestrogen dose equal to or less than that in the second phase, and to a method of oral contraception using said preparation.

10 Claims, No Drawings

MULTI-PHASE COMBINATION-TYPE SEQUENTIAL PREPARATION FOR ORAL CONTRACEPTION AND METHOD OF ORAL CONTRACEPTION

The invention relates to a multi-phase combination-type sequential preparation for oral contraception consisting of 20–22 tablets (daily dose units), each comprising a gestagen and an oestrogen and to a method of oral contraception using said preparation.

Oral contraceptives of the "combination-type" for sequential or cyclic use are generally known, for example the preparations "Lyndiol", "Ovulen", "Anovlar", "Neogynon", "Stediril", "Ovostat" and similar combinations of a gestagen and an oestrogen. Such combination-type preparations consist normally of 20–22 tablets of the same composition for daily dosage (each day one tablet), which is followed by a tablet-free period of 5–7 days which completes the natural female cycle of roughly 28 days. During the tablet-free period, withdrawal bleeding occurs. After the tablet-free period a new cycle is started using the combination-type preparation. The tablet-free period can if required be supplemented by placebos, such as for example is the case with the combination-type preparation "Pregnon 28". Multi-phase combination-type sequential preparations, whereby different quantities of gestagen and/or oestrogen are employed during the different phases, are also known. Thus in U.S. Pat. No. 3,939,264 a description is given of a two-phase combination-type preparation for oral contraception, consisting of 21–23 tablets, where the first 10–12 tablets each comprise a quantity of gestagen, which in activity corresponds with 0.050–0.125 mg of d-norgestrel, and a quantity of oestrogen which corresponds as regards activity with 0.030–0.050 17α-ethinyloestradiol (EE), and each of the following 11–9 tablets contains a quantity of gestagen which is 2–3 times greater than that during the first phase, the quantity of oestrogen remaining the same. An attemps is made in this manner to obtain better adaptation to the natural female cycle, while a constinuous, constant dosage of oestrogen is employed. In this way good contraceptive effect with reduced side effects should be obtained.

A variation on this two-phase combination-type sequential preparation is described in U.S. Pat. No. 3,969,502. The difference here is that the quantity of oestrogen per tablet in the second phase is greater than that in the first phase, with a maximum of two times as great, so that not only the gestagen but also the oestrogen is administered in phased fashion. With this preparation there should be less oestrogen-dependent side effects.

A three-phase combination-type preparation is described in U.S. Pat. No. 3,957,982. This sequential preparation consists of 21 tablets and comprises a first phase of 4–6 tablets each containing a gestagen in a quantity which, as regards activity, corresponds with 0.040–0.090 mg of d-norgestrel, and an oestrogen in a quantity which as regards activity corresponds with 0.020–0.050 mg EE, a second phase of 4–6 tablets each containing a gestagen in a quantity 1–1.5 times that during the first phase, for example 0.050–0.125 mg of d-norgestrel, and an oestrogen in a quantity which is 1–2 fold that during the first phase, for example 0.030–0.050 mg EE, and finally a third phase of 9–11 tablets each containing a quantity of a gestagen which is greater than that during the second phase and not more than three times as great as that during the first phase, for example 0.100–0.250 mg of d-norgestrel, and a quantity of oestrogen which is greater than or equal to that during the first phase, and which is less than or equal to that during the second phase, for example 0.025–0.050 mg EE. As compared with the known two-phase combination-type preparations, the compatibility and/or cycle control should be capable of being improved when using such a three-phase preparation.

In German patent application No. 2 431 704 a description is given of a variant of the said three-phase preparation. The difference here is that in this variant the three phases are taken for roughly the same period (6–8 tablets), preferably 3×7 tablets.

The multi-phase preparations described above illustrate the development, which has already been in progress for some time, in oral contraceptives leading to preparations with a lower content of gestagen and oestrogen. The metabolic changes occurring during the use of oral contraceptives are ascribed mainly to the oestrogenic component. Preparations with a low dose of oestrogen do not, as regards their effectivity, need to be regarded as inferior to higher dosage preparations. However they exibit the shortcoming that cycle control is poorer, which manifests itself in more break-through bleeding and "spotting" and the absence of withdrawal bleeding during the tablet-free period. Such breakthrough bleeding and "spotting" occurs mainly during the second half of the treatment cycle. The reasons are that with these combination-type preparations having a low content of oestrogen and relatively high content of gestagen, the oestrogenic effect on the endometrium is impeded by the gestagen which has an anti-oestrogenic effect. The lack of oestrogenic influence on the endometrium results in more bleeding during administration, and as already pointed out, particularly during the last days of the cyclic treatment.

It is already known that excellent cycle control can be obtained with a two-phase sequential preparation whereby during the first phase exclusively an oestrogen is administered and during the second phase a combination of a gestagen and an oestrogen, e.g. a normophasic preparation such as "Ovanon" or "Fysioquens" (7 tablets with 0.050 mg EE and 15 tablets with 2.5 mg or 1 mg lynestrenol+0.050 mg EE).

In order to obtain adequate effectivity with this type of preparation it is essential during the first phase to employ at least 0.050 mg EE per tablet. With a lower oestrogen content contraceptive reliability is violently disturbed. An attempt was then made, if possible whilst retaining the good properties of the normo-phasic preparation, to impart success to the trend towards preparations with a lower content of oestrogen.

It was then found that if during an initial phase the oestrogen is combined with a low dose of gestagen, during a second phase a lower dose of oestrogen is administered combined with a higher dose of gestagen, and during a third phase a combination is administered which contains a quantity of oestrogen which is equal to or less that that during the second phase, and a quantity of gestagen which is equal to or greater than that during the second phase, a combination-type preparation is obtained which combines excellent cycle control and good contraceptive properties with a low content of oestrogen.

The present invention hence relates to a multi-phase combination-type sequential preparation for oral contraception consisting of 20–22 tablets each containing a gestagen and an oestrogen, and is characterised in that an initial phase consists of 5–8 tablets, each of which contains a low dose of gestagen and a relatively high dose of oestrogen, a second phase of 5–8 tablets each with a gestagen dose which is greater than that during the first phase, and an oestrogen dose which is less than that during the first phase, and a third phase consisting of 5–11 tablets each having a gestagen dose equal to or greater than that during the second phase and an oestrogen dose equal to or less than that during the second phase.

The present invention further relates to a method of oral contraception in which for 20–22 days the tablets of the combination-type preparation according to the invention are administered to a fertile female, said administration being performed according to the prescribed sequence of phases and administering one tablet a day.

All substances with gestagenic action are suitable as gestagen in the preparation according to the present invention, such as for example lynestrenol, desogestrel, norethisteron, norethisteronacetate, ethynodioldiacetate, dl-norgestrel, d-norgestrel, norethynodrel, cingestol and derivatives thereof which are obtained by introducing one or more double bonds, e.g. at the 6(7) location, by substitution, e.g. with chlorine or methyl, at for example the 7th or 11th position, or by preparation of functional derivatives such as for example esters, particularly esters of alkane carboxylic acids with 1–12 C-atoms, ethers such as alkyl (1–4 C)-ethers, tetrahydropyranylether, cyclo-alkyl (5–6 C) ethers, or acetals such as ethylene diacetals or propylene diacetals.

Preferably desogestrel and the 3-oxo derivative of desogestrel are employed as gestagens.

The usual oestrogens, such as EE, mestranol, oestradiol esters and substituted derivates thereof can be employed as oestrogen in the preparation according to the present invention. Preferably EE is employed as oestrogen. If required different gestagens and/or oestrogens can be employed during the different phases.

The amount of gestagen per tablet expressed in mg desogestrel during the first phase is not more than 0.050 mg and is normally between 0.020 mg and 0.050 mg. In the second phase the amount of gestagen per tablet is preferably 1.5–5 times greater than during the first phase and is usually between 0.040 mg and 0.200 mg expressed in mg desogestrel. During the third phase the amount of gestagen is preferably 3–6 times as great as during the first phase and is normally between 0.060 mg and 0.250 mg expressed in mg desogestrel.

The amount of oestrogen per tablet expressed in mg EE is during the first phase less than 0.050 mg and is preferably between 0.030 and 0.045 mg. In the second phase the amount of oestrogen is less than during the first phase and is then preferably between 0.020 and 0.035 mg expressed in mg EE. In the third phase the amount of oestrogen is equal to or less than that during the second phase and is then preferably between 0.015 and 0.030 mg expressed in mg EE.

In this way it is possible to ensure that the total quantity of oestrogen in the 20–22 tablets of one cycle does not exceed the amount which corresponds to 0.750 mg EE. Preferably this total quantity is not greater than 0.700 mg expressed in mg EE. It should be pointed out that with numerous known combination-type sequential preparations the daily dose of oestrogen is normally 0.050 mg EE which, for 20–22 days, gives a total oestrogen quantity of 1.0–1.1 mg EE.

If we look at the ratio between the total amount of gestagen and the total amount of oestrogen in the 20–22 tablets, it can be seen that this ratio too can be of importance. A high ratio figure can on the one hand indicate a small total quantity of oestrogen, but on the other hand can point to a large total quantity of gestagen. Naturally it is important that also the total quantity of gestagen should be as low as possible without causing a deterioration in the contraceptive reliability of the preparation. Preferably the total amount of gestagen in the 20–22 tablets, expressed in mg desogestrel, is between 2 and 4 times larger than the total amount of oestrogen expressed in mg EE.

In this patent application (except for the examples) when reference is made to tablets, this means other oral dosage units as well such as pills, capsules, coated tablets, granules. The oral dosage units are obtained by mixing the desired quantity of gestagen and oestrogen using the normal pharmaceutically acceptable aids such as fillers, binders, disintegration means, colouring agents, flavours and lubricants, and bringing the mixture into the form of a pharmaceutical moulding, or filling capsules therewith.

If required the combination-type preparation according to the invention can be supplemented by a number of placebos (6–10) in order to bridge the period in which no active substances need to be administered, so that the daily habit of swallowing a tablet dose not need to be interrupted and it is only necessary to remember to start a new cycle after withdrawal bleeding, i.e. to start a new packaging unit (strip).

It is recommended that the placebos and the tablets in the three phases be distinguished from each other by giving them different shape and/or colour.

Preferably data indications should be provided on the packagings in which the preparation according to the invention is packed, indicating on what date in the cycle the pharmaceutical moulding corresponding with the date indication should be taken.

The combination-type preparation can be packed in a tube or box or in strip packaging. In the event of a small box being used which can have circular, square or other shape, the tablets are accommodated separately therein, usually along the periphery of the box, and a series of date indications, either adjustable or not, is provided on the box which corresponds with the days on which each of the tablets has to be taken.

Another practical form of packaging is strip packaging or push-through packaging whereby each tablet is sealed in a separate compartment and where, on the strip or the packaging, date indications are provided or other sort of indications which denote the sequence in which the tablets should be taken.

The invention will now be explained with the aid of the following examples, which are preferred specific embodiments of the invention and are to be construed as merely illustrative and not limitative as to the remainder of the disclosure in any way whatsoever.

EXAMPLE I

Composition of Tablets

In the first phase (7 tablets)
 0.025 mg desogestrel
 0.040 mg EE
 8.000 mg potato starch
 2.400 mg polyvinyl pyrrolidone
 0.800 mg stearic acid 0.800 mg silica
0.080 mg di-α-tocopherol
make up to 80.000 mg with lactose.
In the second and third phases (14 tablets)
  0.125 mg desogestrel
  0.030 mg EE
  8.000 mg potato starch
  2.400 mg polyvinyl pyrrolidone
  0.800 mg stearic acid
  0.800 mg silica
  0.080 mg dl-α-tocopherol
  make up to 80.000 mg with lactose.

EXAMPLE II

Composition of Tablets

Same as in Example I, except that in the second and third phases 0.025 mg EE is used instead of 0.030 mg EE.

EXAMPLE III

Composition of Tablets

In the first phase (7 tablets)
  0.050 mg desogestrel
  0.040 mg EE
  16.000 mg maize starch
  1.900 mg polyvinyl pyrrolidone
  1.500 mg talc powder
  0.080 mg magnesium stearate
  make up to 80.000 mg with lactose.
In the second phase (7 tablets)
  0.100 mg desogestrel
  0.030 mg EE
  and otherwise identical with the composition in the first phase;
In the third phase (7 tablets)
  0.200 mg desogestrel
  0.020 mg EE
  and otherwise identical with the composition in the preceding phases.

EXAMPLE IV

Composition of Tablets

In the first phase (7 tablets)
  0.025 mg desogestrel
  0.040 mg EE
  8.000 mg potato starch
  2.400 mg polyvinyl pyrrolidone
  0.800 mg stearic acid
  0.800 mg silica
  0.080 mg dl-α-tocopherol
  make up to 80.000 mg with lactose.
In the second phase (7 tablets)
  0.075 mg desogestrel
  0.030 mg EE
  and otherwise identical with the composition in the first phase.
In the third phase (7 tablets)
  0.125 mg desogestrel
  0.025 mg EE
  and otherwise identical with the composition in the preceding phases.

EXAMPLE V

Composition of Tablets

In the first phase (7 tablets)
  0.040 mg desogestrel
  0.040 mg EE
  5.000 mg potato starch
  2.000 mg polyvinyl pyrrolidone
  0.050 mg dl-α-tocopherol
  0.250 mg magnesium stearate
  make up to 50.000 mg with lactose.
In the second phase (7 tablets)
  0.075 mg desogestrel
  0.030 mg EE
  and otherwise identical with the composition in the first phase.
In the third phase (7 tablets)
  0.125 mg desogestrel
  0.030 mg EE
  and otherwise identical with the composition in the preceding phases.

EXAMPLE VI

Composition of Coated Tablets

| In the first phase (7 tablets) | |
|---|---|
| | 0.050 mg 3-oxo-desogestrel |
| | 0.040 mg EE |
| | 16.000 mg maize starch |
| | 1.900 mg polyvinyl pyrrolidone |
| | 1.500 mg talc powder |
| | 30.510 mg lactose |
| | 50.000 mg |
| which is processed together with a normal sugar mixture to give coated tablets of roughly 80 mg. | |

In the second phase (7 tablets)
  0.075 mg 3-oxo-desogestrel
  0.030 mg EE
  and otherwise identical with the composition in the first phase.
In the third phase (7 tablets)
  0.150 mg 3-oxo-desogestrel
  0.025 mg EE
  and otherwise identical with the composition in the preceding phases.

EXAMPLE VII

Composition of Tablets

In the first phase (5 tablets)
  0.025 mg desogestrel
  0.040 mg EE
  8.000 mg potato starch
  2.400 mg polyvinyl pyrrolidone
  0.800 mg stearic acid
  0.800 mg silica
  0.080 mg dl-α-tocopherol
  make up to 80.000 mg with lactose
In the second phase (7 tablets)
  0.075 mg desogestrel
  0.030 mg EE
  and otherwise identical with the composition in the first phase.
In the third phase (9 tablets)
  0.125 mg desogestrel
  0.025 mg EE
  and otherwise identical with the composition in the preceding phases.

EXAMPLE VIII

Composition of Tablets

In the first phase (6 tablets)

0.040 mg desogestrel
0.040 mg EE
0.012 mg indogotine
8.000 mg potato starch
2.400 mg polyvinyl pyrrolidone
0.800 mg stearic acid
0.080 mg dl-α-tocopherol
make up to 80.000 mg with lactose
In the second phase (8 tablets)
0.075 mg desogestrel
0.030 mg EE
and otherwise identical with the composition in the second phase, whereby however 0.012 mg indogotine is replaced by 0.020 mg sun yellow FCF.
In the third phase (7 tablets)
0.150 mg desogestrel
0.025 mg EE
and otherwise identical with the composition in the preceding phases, whereby however the colouring agent is omitted.

EXAMPLE IX

A preparation according to Example I was administered to 720 fertile women daily for 7 days (first phase) and daily for the following 14 days (second and third phase) per woman. The subsequent 7 days during which the menstrual bleeding occurred remained without administration. This regimen of administration was maintained for about 8 months, resulting in a total number of 5363 treatment cycles.

During the entire treatment period no pregnancies occurred. Cycle control was excellent. The incidence of breakthrough bleedings and spottings was low. Also other side effects were on a low level.

EXAMPLE X

A preparation according to Example III was administered to 710 fertile women daily for 7 days (first phase), daily for the following 7 days (second phase) and daily for the subsequent 7 days (third phase) per woman. Another 7 days during which the menstrual bleeding occurred remained without administration. This regimen of administration was maintained for about 6 months, resulting in a total number of 3982 treatment cycles.

During the entire treatment period no pregnancies occurred. Cycle control was excellent. The number of drop-outs was very small indicating the low incidence of side effects.

I claim:

1. A multi-phase combination-type sequential preparation for oral contraception consisting of 20-22 tablets each containing a gestagen and an oestrogen characterized in that a first phase consists of 5-8 tablets, each of which contains a low dose of gestagen and a relatively high dose of oestrogen, a second phase of 5-8 tablets each having a gestagen dose which is greater than that during the first phase and an oestrogen dose which is smaller than that in the first phase, and a third phase of 5-11 tablets each of which has a gestagen dose equal to or greater than that during the second phase and an oestrogen dose equal to or less than that in the second phase, wherein the gestagen is selected from the group consisting of desogestrel and the 3-oxo derivative thereof, and the oestrogen is ethinyloestradiol, the amount of gestagen in the first phase tablet being less than or equal to 0.050 mg, the amount of oestrogen in said first phase tablet being less than 0.050 mg, the amount of gestagen in the three phases being in the ratio of 1:1.5-5:3-6.

2. Preparation according to claim 1, characterized in that the amount of oestrogen per tablet expressed in mg ethinyloestradiol in the first phase is between 0.030 and 0.045, in the second phase between 0.020 and 0.035 and in the third phase between 0.015 and 0.030.

3. Preparation as in claim 2, characterized in that the total amount of oestrogen in the 20-22 tablets expressed in mg ethinyloestradiol is less than 0.750.

4. Preparation as in claim 1, characterized in that the total amount of gestagen in the 20-22 tablets expressed in mg desogestrel is between 2 and 4 times as great as the total amount of oestrogen expressed in mg ethinyloestradiol.

5. Preparation as in claim 1, characterized in that the first phase consists of 7 tablets each of which contains, as the gestagen, 0.025 mg desogestrel and, as the oestrogen, 0.040 mg ethinyloestradiol, the second phase consists of 7 tablets each containing 0.125 mg desogestrel and 0.030 mg ethinyloestradiol, and the third phase consists of 7 tablets each of which contains the same amount of gestagen and oestrogen as in the second phase.

6. Preparation as in claim 1, characterized in that the first phase consists of 7 tablets each of which contains, as the gestagen, 0.025 mg desogestrel and, as the oestrogen, 0.040 mg ethinyloestradiol, the second phase consists of 7 tablets each of which contains 0.125 mg desogestrel and 0.025 mg ethinyloestradiol, and the third phase consists of 7 tablets each of which contains the same amount of gestagen and oestrogen as in the second phase.

7. Preparation as in claim 1, characterized in that the first phase consists of 7 tablets each of which contains, as the gestagen, 0.050 mg desogestrel and, as the oestrogen, 0.040 mg ethinyloestradiol, the second phase consists of 7 tablets each of which contains 0.100 mg desogestrel and 0.030 mg ethinyloestradiol, and the third phase consists of 7 tablets each of which contains 0.200 mg desogestrel and 0.020 mg ethinyloestradiol.

8. Preparation as in claim 1, characterized in that the first phase consists of 7 tablets each of which contains, as the gestagen, 0.025 mg desogestrel and, as the oestrogen, 0.040 mg ethinyloestradiol, the second phase consists of 7 tablets each of which contains 0.075 mg desogestrel and 0.030 mg ethinyloestradiol, and the third phase consists of 7 tablets each of which contains 0.125 mg desogestrel and 0.025 mg ethinyloestradiol.

9. A method of oral contraception which comprises orally administering the tablets of the combination-type preparation as defined in any one of claims 2, 3, 4, 5, 6, 7, 8 or 1 to a fertile female for 20-22 days, said tablets being administered according to the prescribed sequence of phases while administering one tablet a day.

10. Preparation according to claim 3, wherein the amount of oestrogen is less than 0.700 mg of ethinyloestradiol.

* * * * *